(12) United States Patent
Maack

(10) Patent No.: US 9,782,134 B2
(45) Date of Patent: Oct. 10, 2017

(54) LESION IMAGING OPTIMIZATION USING A TOMOSYNTHESIS/BIOPSY SYSTEM

(75) Inventor: Hanns-Ingo Maack, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 576 days.

(21) Appl. No.: 13/703,647

(22) PCT Filed: Jun. 20, 2011

(86) PCT No.: PCT/IB2011/052688
§ 371 (c)(1),
(2), (4) Date: Dec. 12, 2012

(87) PCT Pub. No.: WO2012/001572
PCT Pub. Date: Jan. 5, 2012

(65) Prior Publication Data
US 2013/0090553 A1 Apr. 11, 2013

(30) Foreign Application Priority Data

Jun. 28, 2010 (EP) .................................. 10167521

(51) Int. Cl.
*A61B 6/00* (2006.01)
*A61B 6/02* (2006.01)
(Continued)

(52) U.S. Cl.
CPC ............. *A61B 6/022* (2013.01); *A61B 6/025* (2013.01); *A61B 6/12* (2013.01); *A61B 6/502* (2013.01);
(Continued)

(58) Field of Classification Search
CPC .......... G03B 42/02; H05G 1/26; A61B 6/022; A61B 6/025; G06T 7/0022; G06T 7/004
(Continued)

(56) References Cited

U.S. PATENT DOCUMENTS 5,349,954 A 9/1994 Tiemann et al.
5,852,646 A * 12/1998 Klotz .................... G06T 11/008
378/8
(Continued)

FOREIGN PATENT DOCUMENTS

JP 7163551 A 6/1995
JP 200170248 A1 3/2001
(Continued)

OTHER PUBLICATIONS

Carr et al, "Stereotactic Localization of Breast Lesions: How It Works and Methods to Improve Accuracy", http://radiographics.rsna.org/content/21/2/463.Full, Radio Graphics, vol. 21, 2001, pp. 463-473.

*Primary Examiner* — Amanda Lauritzen Moher

(57) ABSTRACT

The invention relates to a medical tomosynthesis system (10) having an interventional device (15) and an image acquisition device (11, 12) for acquiring images of a subject volume in a plurality of angular positions around the subject volume. In the system, a three-dimensional geometrical model of the interventional unit is used to identify the projection angles of the image acquisition device that actually can be used. Preferably, this three-dimensional model is achieved by reconstructing it from projection images acquired with the X-ray image acquisition device. The invention also relates to a method for acquiring images with such a system.

32 Claims, 5 Drawing Sheets

(51) Int. Cl.
  *A61B 6/12* (2006.01)
  *A61B 10/02* (2006.01)
  *A61B 6/04* (2006.01)
  *A61B 34/10* (2016.01)
(52) U.S. Cl.
  CPC ............ *A61B 6/5205* (2013.01); *A61B 6/582* (2013.01); *A61B 10/0233* (2013.01); *A61B 6/0414* (2013.01); *A61B 6/4494* (2013.01); *A61B 2034/107* (2016.02)
(58) Field of Classification Search
  USPC ............... 600/407, 425, 427; 378/21, 23, 41
  See application file for complete search history.

(56) References Cited

U.S. PATENT DOCUMENTS

| | | | |
|---|---|---|---|
| 6,256,370 B1* | 7/2001 | Yavuz | 378/22 |
| 8,194,819 B2 | 6/2012 | Eliasson | |
| 2001/0029334 A1 | 10/2001 | Graumann et al. | |
| 2002/0114423 A1 | 8/2002 | Grass et al. | |
| 2006/0241727 A1 | 10/2006 | Dowlatshahi | |
| 2007/0021668 A1* | 1/2007 | Boese | A61B 6/12 600/424 |
| 2007/0225600 A1 | 9/2007 | Weibrecht et al. | |
| 2008/0045833 A1* | 2/2008 | Defreitas et al. | 600/429 |
| 2008/0198966 A1 | 8/2008 | Hjarn et al. | |
| 2009/0088629 A1 | 4/2009 | Groszmann et al. | |
| 2009/0225935 A1 | 9/2009 | Eliasson | |
| 2009/0304159 A1 | 12/2009 | Meer | |
| 2012/0022358 A1 | 1/2012 | Fischer | |
| 2014/0073913 A1 | 3/2014 | Defreitas et al. | |
| 2014/0241500 A1 | 8/2014 | Yasuda | |
| 2015/0073298 A1 | 3/2015 | Finke | |
| 2015/0342579 A1 | 12/2015 | Heske | |
| 2016/0089098 A1 | 3/2016 | Nakayama | |
| 2016/0128787 A1 | 5/2016 | Gunee | |
| 2016/0183887 A1 | 6/2016 | Toba | |
| 2016/0183898 A1 | 6/2016 | Cormican | |
| 2016/0310215 A1 | 10/2016 | Palma | |

FOREIGN PATENT DOCUMENTS

| | | |
|---|---|---|
| JP | 2001217765 A | 8/2001 |
| JP | 2009526618 A | 7/2009 |
| WO | WO2007095330 | 8/2007 |

\* cited by examiner

LESION IMAGING OPTIMIZATION USING A TOMOSYNTHESIS/BIOPSY SYSTEM

FIELD OF THE INVENTION

The present invention relates to a medical tomosynthesis system, a method for acquiring medical images and a computer program for executing such a method.

BACKGROUND OF THE INVENTION

Regular stereoscopic guidance is done using two pre-defined angular positions of an X-ray tube for X-ray images, wherein one angular position is left and the other one is right of the centre position. The two coordinates of a specific lesion in the two images can be used to identify all three coordinates of the lesion in the object of examination. To identify the z-position of a lesion, a cross hair cursor has to be set in the two stereo images. The z-position can be calculated from these values. However, the accuracy of the x-position (horizontal) may propagate into an uncertain z-position. A tissue sample can be taken at this position using a biopsy needle.

In tomosynthesis imaging several x-ray images are acquired in different angles from a subject volume, such as a part of the human body. From this set of projection images a three-dimensional data set can be derived from which two-dimensional images can be reconstructed.

Such a tomosynthesis imaging for diagnosing breast cancer is described in US 2007/0225600 A1. This document relates to a system and a method for the investigation of a body volume, particularly for the diagnosis of breast cancer. A sequence of X-ray projections from different directions is produced by a rotatable X-ray source and a stationary digital X-ray detector. From these projections, a set of sectional images is calculated by tomosynthesis. A physician may indicate a suspicious structure on a reference image that is derived from one of the projections or sectional images and displayed on a monitor. The computer may then locate the structure on all sectional images and calculate the similarity of a corresponding image feature. The sectional image at which the similarity is strongest then indicates the depth at which the structure is positioned in the body volume. Based on this information, a biopsy device with a needle can be advanced into the body volume until it reaches the suspicious structure.

However, in these systems some of the projection images may show a shadow of the biopsy device if the biopsy device is located within the X-ray beam. FIG. 1 shows a stereoscopic or tomosynthetic imaging system. On the upper left side, the system is shown in a right angular position, and below, there is schematically shown a resulting projection image which illustrates some circular lesions, a shadow of the biopsy needle holder 1, a shadow of the biopsy needle 2 and part of an opening 3 of a biopsy paddle. On the upper right side, the system is shown in its left angular position, and below, there is also schematically shown a resulting projection image which also illustrates some circular lesions and the shadow of the biopsy unit, i.e. the biopsy needle holder shadow 1, the biopsy needle shadow 2 and the shadow of the opening 3.

SUMMARY OF THE INVENTION

It is an object of the invention to provide an improved medical tomosynthesis system and a method for acquiring medical images.

This object is solved with the medical tomosynthesis system and the method for acquiring medical images according to the independent claims.

According to an embodiment of the invention a medical tomosynthesis system is provided, the system comprising an interventional device, preferably a biopsy needle holder and/or a biopsy needle, for intervening into a subject volume; an image acquisition device for acquiring images of the subject volume in a plurality of angular positions around the subject volume; geometric data means for providing geometric data of the interventional device, the geometric data preferably defining the outer shape of the interventional object; a processor for determining, depending on the geometric data received from the geometric data means, a plurality of angular positions at which the image acquisition device is allowed to acquire images.

In this embodiment, compared to the regular stereoscopic guidance, the two exposures are replaced by N exposures left of and M exposures right of the center position. Compared to a regular Digital Breast Tomosynthesis scan, some exposures will not be taken. These are for example the ones from the center position where the biopsy needle and the biopsy holder (biopsy unit) would cast a shadow onto the detector. According to this embodiment a three-dimensional geometrical model of the biopsy unit is used to identify the projection angles that actually can be used. This provides the benefits of a better three-dimensional visualization of the target of biopsy. Further, a dose saving in respect to regular Digital Breast Tomosynthesis can be achieved, because no X-rays are applied that do not contribute to the visualization of the region of interest (the location of a lesion or microcalcifications). Further, the field of use is wider, also behind the compression plate in some of the views. The embodiment allows a 3D definition of the region of interest as target for biopsy with a simplified workflow, because the shadowing has not to be considered in the final 3D model of the region of interest.

According to another embodiment of the invention, the processor is adapted for re-determining the plurality of angular positions when a position of the interventional device changes. The biopsy unit has some movable parts. The useful projection angles may vary with the position of the biopsy needle or the region of interest. Within the needle guidance procedure, all these coordinates are well known within the controller unit. Using these coordinates, the prepared 3D model can be mapped to the current position and the meaningful tube angulation positions can be derived.

According to a further embodiment, the geometric data means comprises an image processor for acquiring the geometric data of the interventional device from images acquired by the image acquisition device. Additionally or alternatively thereto, the geometric data means may be a storage medium for receiving, storing and providing the geometric data. Optionally, this data can be entered into the storage medium by a scanner for scanning a design drawing of the interventional device and for providing the storage medium with the geometric data.

The gist of the invention may be seen in that a medical tomosynthesis system is provided in which a three-dimensional geometrical model of the biopsy unit is used to identify the projection angles that actually can be used. Preferably, this three-dimensional model is achieved by reconstructing it from projection images acquired with the X-ray imaging device.

These and other aspects of the invention will be apparent from and elucidated with reference to the embodiments described hereafter.

DETAILED DESCRIPTION OF EMBODIMENTS

The present invention is directed to a medical tomosynthesis system which can be used for diagnosing breast cancer and for guiding an interventional tool or device, such as a biopsy needle, to a lesion for taking a tissue sample. Tomosynthesis is a medical imaging method which acquires several x-ray images at different angles from a subject volume, such as a human breast. From this set of projection images a three-dimensional (3D) data set is derived. This 3D data set is the basis for reconstructing two-dimensional (2D) slices or slabs at desired positions and with a desired orientation, wherein the slices or slabs are usually in parallel to the xy-plane, xz-plane or yz-plane. One slice represents a very thin volume element in form of a plane being 0.5 to 1 mm thick. One slab represents an average of some adjacent slices and corresponds to a volume element of some mm or cm of the subject volume. Only the first imaging for determining the 3D model of the biopsy unit is done as a regular tomosynthesis examination and usually done with the biopsy needle in place. All the following scans within the examination will use the useful projection angles.

Figure 1:
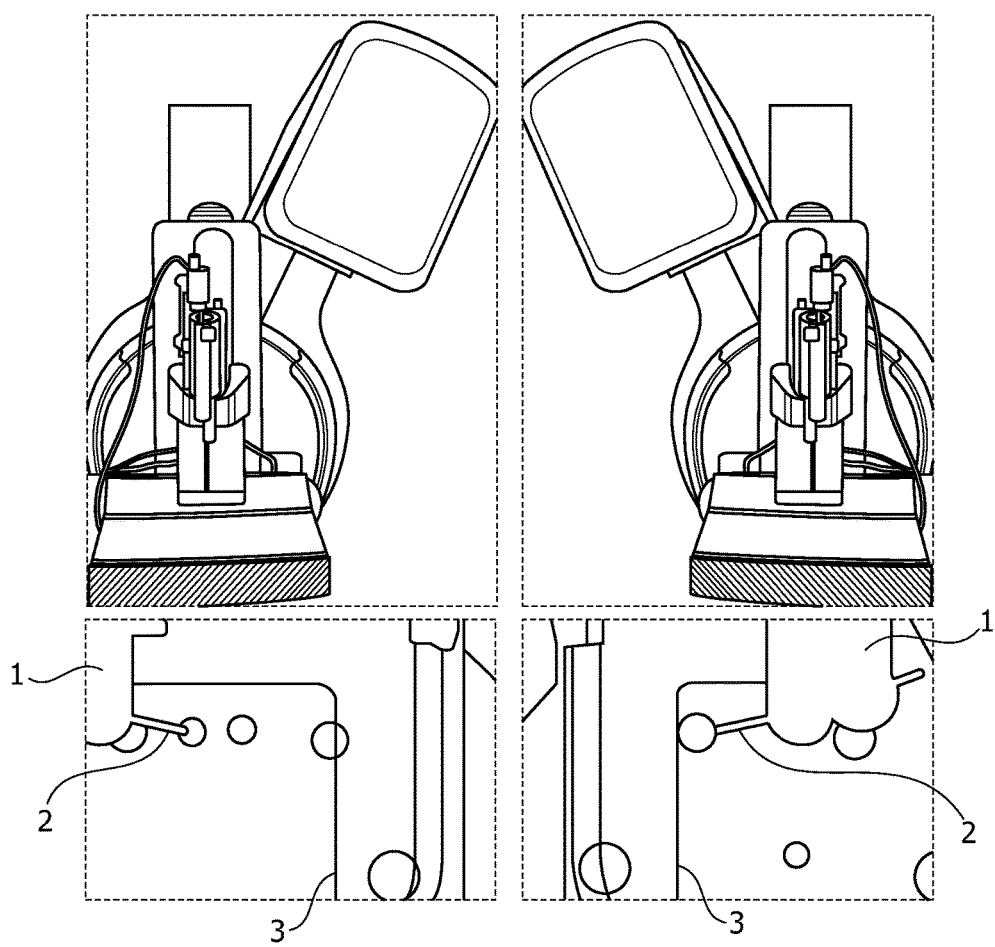
FIG. 1 shows a view in a right angulation and a view in a left angulation of stereoscopic imaging, wherein below, partial sketches of the two images of the corresponding positions are shown.
Figure 2:
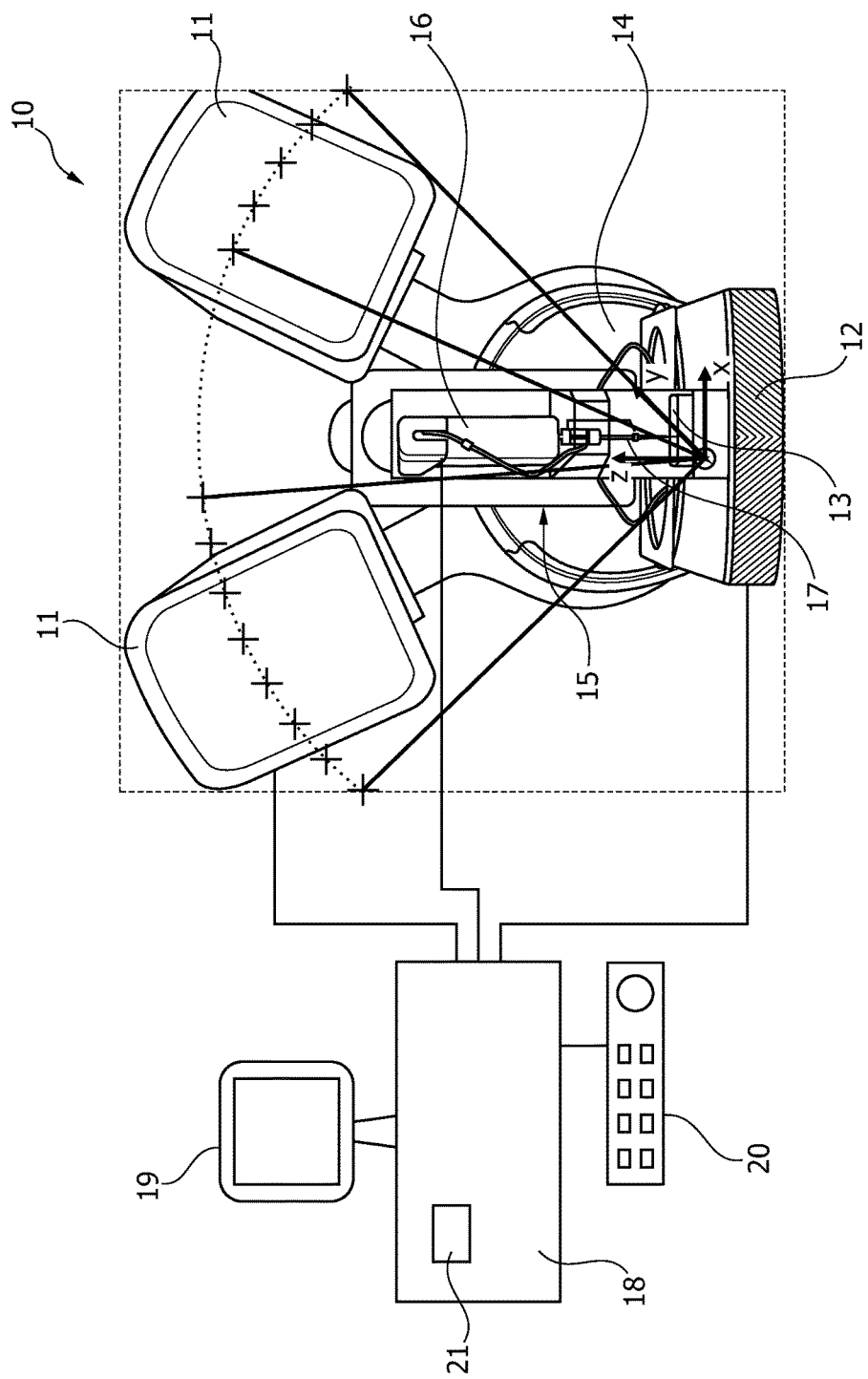
FIG. 2 shows medical tomosynthesis system according to an embodiment of the invention.

FIG. 2 shows the tomosynthesis system 10 according to an embodiment of the invention. For explanatory reasons, a coordinate system is shown in FIG. 2 which is a known Cartesian coordinate system having the axes x, y and z. The medical tomosynthesis system 10 comprises an X-ray imaging device with an X-ray source 11 and an X-ray detector 12. The X-ray detector 12 is a digital, flat X-ray detector which detection surface is substantially parallel to the xy-plane. The breast or subject volume to be diagnosed and/or treated (not shown in FIG. 2) is usually placed directly onto the X-ray detector 12. In between the X-ray source 11 and the X-ray detector 12 there is provided a compression plate 13 which is shown in more detail in FIG. 3. The compression plate 13 is transparent to X-rays and a flat biopsy paddle which compresses and fixates a part of the breast to be diagnosed and/or treated. The compression plate 13 is arranged substantially in parallel to the xy-plane and mounted to a base frame 14 in a certain adjustable distance above the X-ray detector 12, wherein the distance is chosen such that a human breast can be compressed, accordingly.

The X-ray source 11 is preferably a single X-ray tube mounted via a rotatable frame to the base frame 14 and movable along a trajectory which is preferably a circular arc shown as a dotted line in FIG. 2. During the movement of the X-ray source 11 along the trajectory the X-ray source 11 is always oriented such that the X-rays are radiated towards the breast and the breast remains in the center of the irradiation before the X-rays hit the X-ray detector 12. The center of the arc shape preferably corresponds to the center of the shown coordinate system, wherein the movement of the X-ray source 11 leads to a rotation of the X-ray source longitudinal direction (direction of the center X-ray beam) within the xz-plane about the y-axis. In FIG. 2, the same single X-ray tube 11 is shown in two positions, in a left position in which the emitted X-ray beam is inclined to the left with respect to the yz-plane and in a right position in which the emitted X-ray beam is inclined to the right with respect to the yz-plane. Alternatively, it is possible to provide two X-ray tubes 11.

Figure 4:
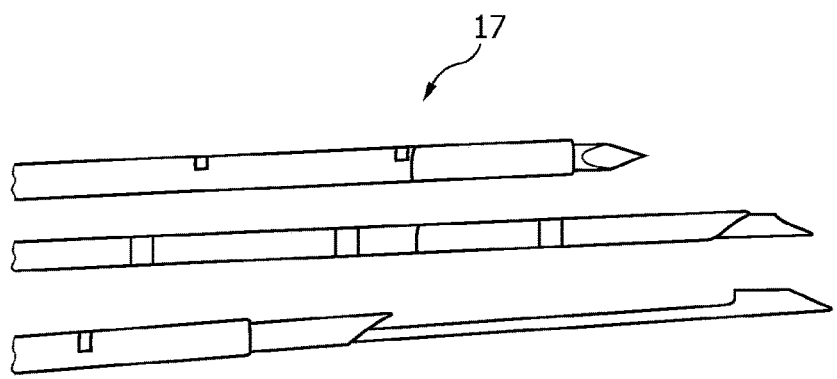
FIG. 4 shows a plurality of biopsy needles.

Basically in between the X-ray source 11 and the compression plate 13, there is provided a biopsy unit 15 comprising a biopsy needle holder 16 and a biopsy needle 17. The biopsy unit 15 shall include all the necessary hardware for a biopsy examination, wherein the main parts are the biopsy needle holder 16 and biopsy needles 17, but can also include the compression plate 13. There is a plurality of biopsy needles 17 provided having different shapes and sizes, as shown in FIG. 4. Each one of the biopsy needles 17 can be mounted into and are fixedly held by the biopsy needle holder 16. Preferably, only a single one of the biopsy needles 17 at one time can be attached to the biopsy needle holder 16 depending on which one is needed for the diagnosis/biopsy.

When the breast is irradiated with a beam of X-rays from the X-ray source 11, a projection image is produced on the X-ray detector 12. At several intermediate positions along the trajectory, the X-ray source 11 emits X-rays towards the X-ray detector 12, which produces projection images of the breast onto the X-ray detector 12 from different directions. The intermediate positions are located in regular intervals along the trajectory, e.g. 10° to 50° along the shown circular arc shape. A processor 18 is provided with these projection images and reconstructs a 3D model from the taken projection images. Further, from this 3D model, the processor 18 calculates 2D slices (sectional images) through the breast for example in parallel to the xy-plane at different z positions. The calculation may be done according to the known tomosynthesis reconstruction methods. The slices at desired z positions and or the projection images can be displayed on a display 19 connected with the processor 18. Further, an input device 20 for manipulating the tomosynthesis system 10 and for inputting data into the processor 18 is provided. The processor 18 is connected to both, the X-ray source 11 and the X-ray detector 12. Further, geometric data means 21 are provided, wherein the geometric data means 21 can be a storage medium, such as a memory chip, a hard drive or a flash drive. Alternatively the geometric data means 21 can be, or additionally the geometric data means 21 can comprise an image processor. The functionality of the geometric data means 21 is explained below.

Figure 3:
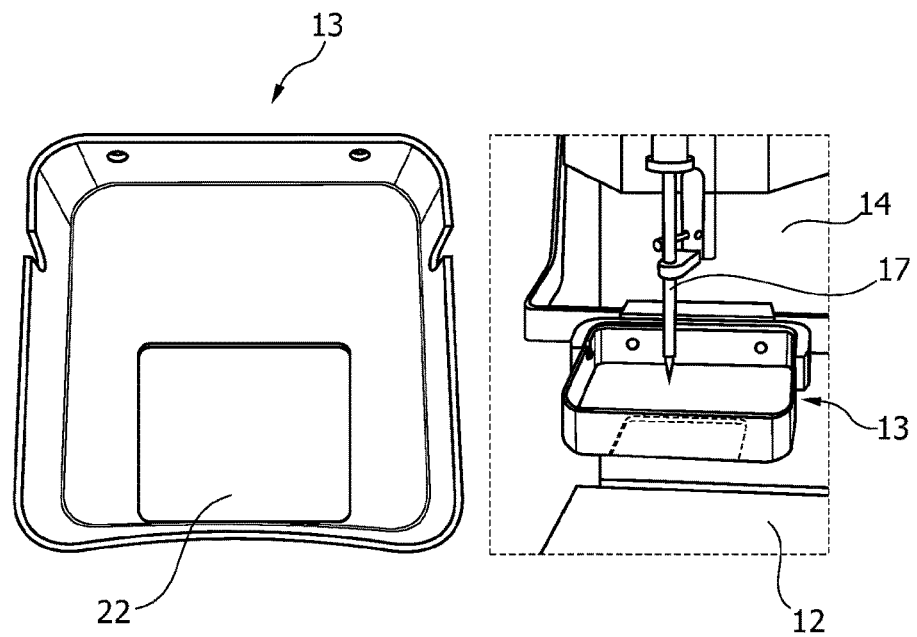
FIG. 3 shows the compression plate and the biopsy needle in more detail.

FIG. 3 shows the compression plate 13, and the combination of the compression plate 13 and the biopsy needle 17 in more detail. The compression plate 13 is basically a square (100×100 mm) or rectangular biopsy paddle having an opening 22 with the size of 40×50 mm. The biopsy needle 17 can be guided through the opening 22 for intervening into the breast towards the lesion for taking a tissue sample. During the intervention, the herein described tomosynthesis system 10 can assist the physician by localizing the biopsy needle 17 as described below.

FIG. 4 shows a plurality of biopsy needles 17. The biopsy needles 17 differentiate in size, diameter and/or shape. The physician can decide during the intervention which needle is the one most suitable.

Figure 5:
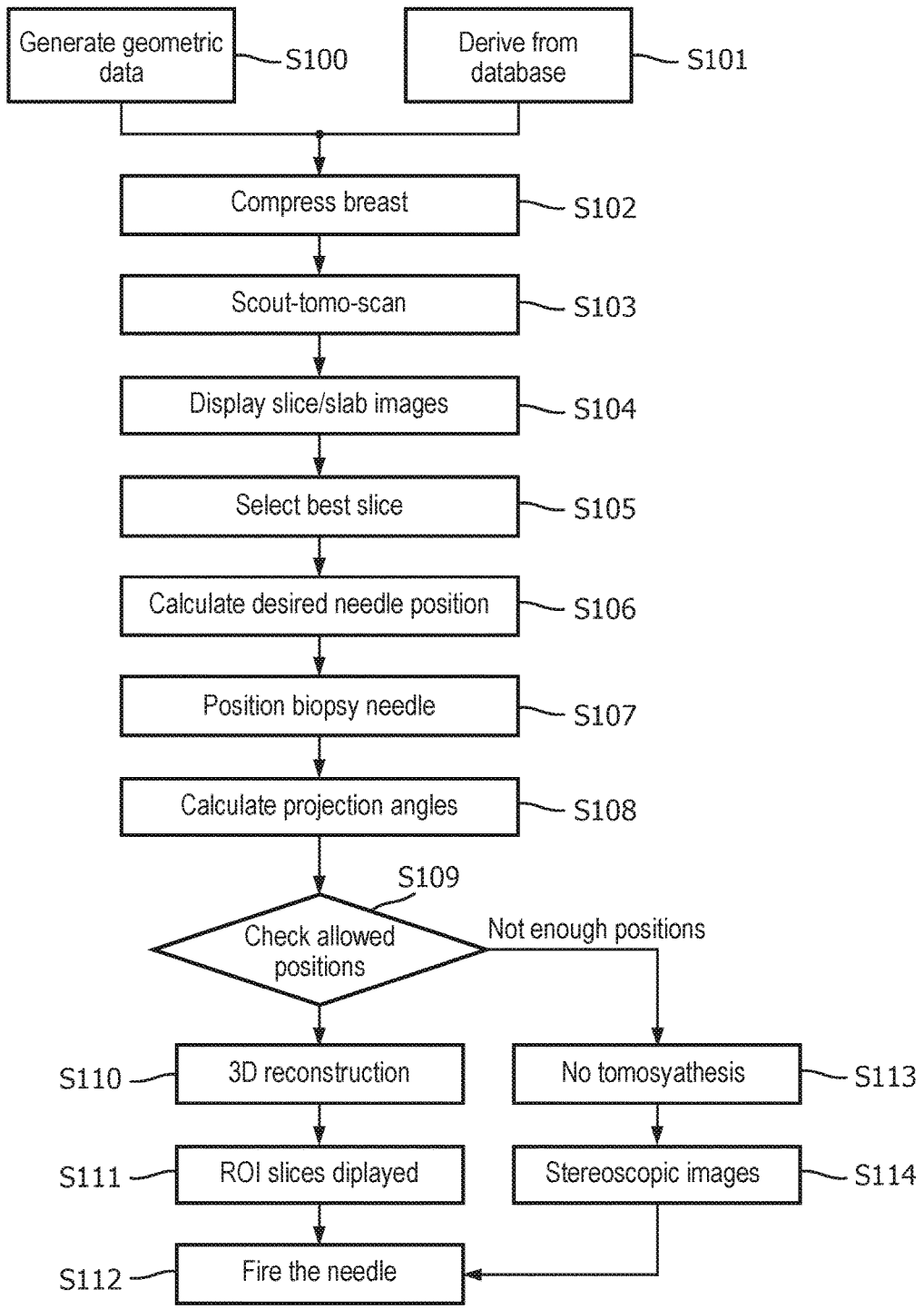
FIG. 5 shows a flow chart of the tomosynthesis method according to an embodiment of the invention.
Figure 6:
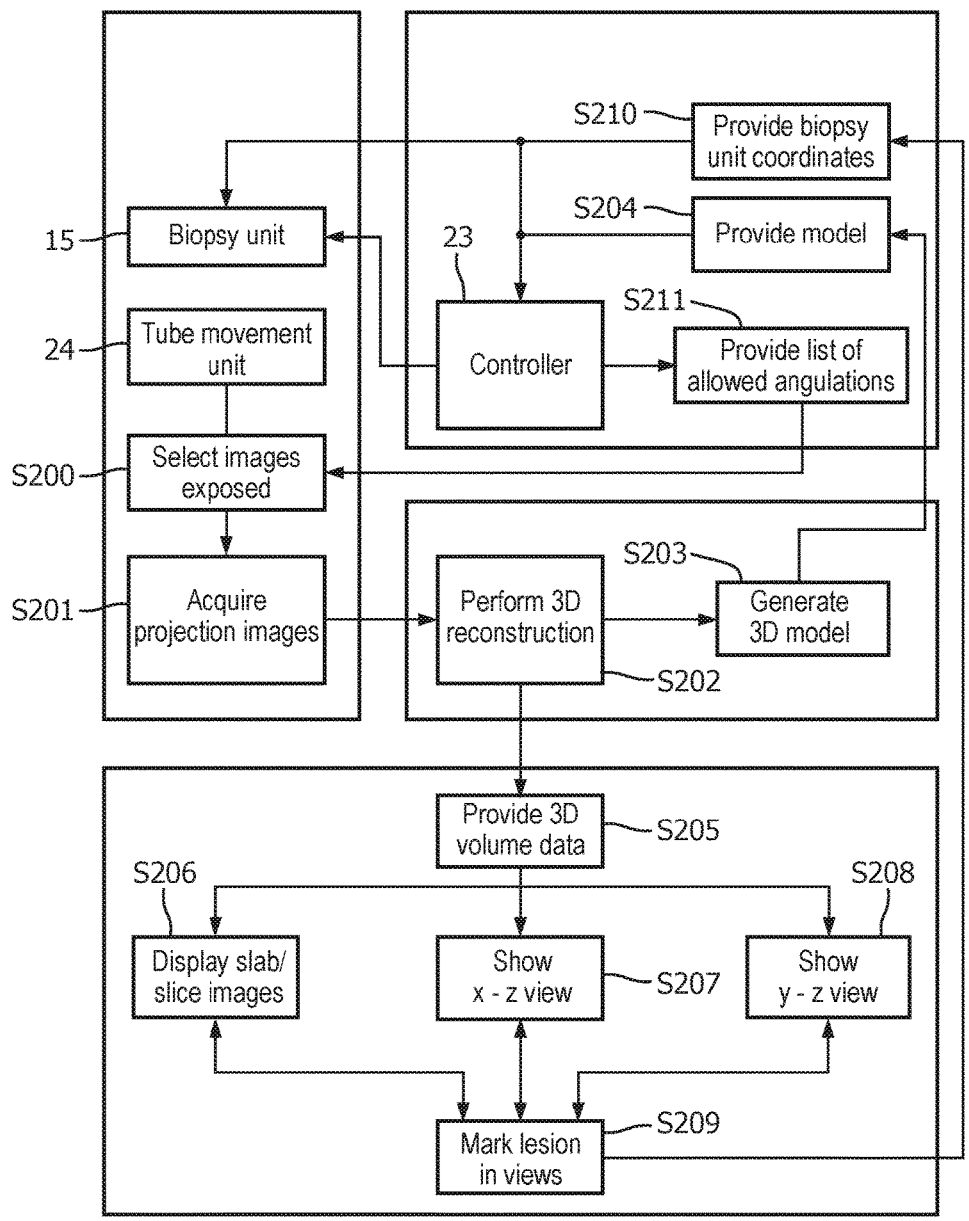
FIG. 6 shows a block diagram of the tomosynthesis system and method according to an embodiment of the invention.

FIG. 5 is a flow chart showing a method for acquiring tomosynthesis images according to an embodiment of the invention, and FIG. 6 is a block diagram which illustrates the interaction of several functional blocks of the tomosynthesis system 10 according to an embodiment of the invention. In FIG. 6, the shown blocks represent functional interactions of the different modules, wherein exemplary the blocks 15, 24, S200, S201 are grouped in a mammography system, the blocks 23, S204, S210, S211 are grouped in a processor module, the blocks S202, S203 are grouped in a 3D reconstruction module (which may also be executed by the processor), and the blocks S205, S206, S207, S208, S209 are grouped in a viewing module.

At the beginning of the herein described tomosynthesis-based biopsy, a geometric model in form of geometric data of the biopsy unit(s) with all available needles is defined. The geometric model is an exact definition of the outer shape of the biopsy unit and may additionally include the position with respect to the coordinate system shown in FIG. 2. Preferably, the geometric model is a 3D voxel model which is a model composed of values representing a volume element at a certain node within a regular 3D grid.

A first possibility for generating the geometric model is shown by step S100 (see FIG. 5) or steps S200-S204 (see FIG. 6), in which the following calibration procedure is conducted. First in this calibration routine, the biopsy unit 15 is placed in a known position with the biopsy needle 17 inserted into the biopsy needle holder 16 and without the breast placed in between the X-ray source 11 and the X-ray detector 12. It is preferable to place the biopsy unit 15 into a "worst case position" in which as much of the volume of the biopsy unit 15 is located in between the X-ray source 11 and the X-ray detector 12 (in the X-ray beam), such that the largest volume of the 3D model of the biopsy unit 15 can be determined. This positioning of the biopsy unit 15 can be conducted by a controller 23 which is represented by the processor 18 or part of it. Then, a tomosynthesis is conducted with all possible angulations of the X-ray source 11. In detail, a tube movement unit 24 moves the X-ray source 11 along the trajectory shown as the dotted arc in FIG. 2 between the outermost positions of the trajectory. In the left outermost position of the X-ray source 11, the longitudinal direction (along emitting direction) of the X-ray source 11 forms an angle of for example −25° with the z-axis. In the right outermost position, the longitudinal direction of the X-ray source 11 forms an angle of for example 25° with the z-axis. During the movement of the X-ray source 11 along the trajectory, selected images are exposed in step S200 (see FIG. 6). In this calibration procedure, the "selected images" are all images at the different angular positions (intermediate positions) the image acquisition device is able to take. In these positions, the X-ray detector 12 acquires projection images at the selected angular positions in step S201. From this set of projection images, a 3D reconstruction is done on basis of the projection images in step S202. A 3D reconstruction for all z-positions up to the entrance window of the tube is done. In the following step S203, a 3D model of the biopsy unit 15 is generated from the 3D reconstruction (in this case the calibration image) by an image processor. The metal/plastic parts in the 3D volume are segmented, wherein this is the geometric model of the biopsy unit. The geometric model of the compression plate 13 can be achieved in a similar way, if necessary. In step S204, the 3D model of the biopsy unit 15 in form of geometric data is provided, e.g. stored in a storage medium. In FIG. 6, the steps S203 and S204 are conducted by the geometric data means 21 introduced in connection with FIG. 2. This procedure could be repeated for several different biopsy needles 17. Then, each configuration of biopsy needle holder 16 and biopsy needle 17 is associated to a respective data set within a stored data base for the geometric data, i.e. there exist several different 3D models in S204. Later on, when the physician decides to interchange the biopsy needle 17 during the intervention, the physician could be provided with the possibility to choose the appropriate data set for the newly used biopsy needle 17 manually by means of the input device 20. Alternatively, the biopsy unit 15 could be provided with detection means for automatically detecting which one of the biopsy needles 17 out of the plurality of biopsy needles 17 is currently attached to the biopsy needle holder 16. These detection means could be realized by providing the biopsy needles 17 with a bar code or other optical markings or some kind of surface coding (grooves, bumps), and to provide the biopsy needle holder 16 in the area where the biopsy needle 17 is inserted into it with an optical or with a sensing detector. Also, a magnetic coding could be realized.

Alternatively, the geometrical model can be generated by inputting the geometrical data into the geometric data means 21, as shown by step S100 (see FIG. 5). This is realized in practice by deriving the information from technical drawings of the biopsy unit 15, which are scanned by a scanner (not shown) or which are provided by the manufacturer of the biopsy unit 15 in form of a data base either online or on a data carrier, or which are inputted (via the input device 20) by a user into the geometric data means 21. With respect to FIG. 6, this would mean that the 3D model is provided right from the start in step S204 and that the steps prior to this one may be omitted. Also, in this connection it is possible that a plurality of data sets is provided each being associated to a different biopsy needle 17. As mentioned above, there is either the possibility that the physician chooses the appropriate data set manually according to the newly used biopsy needle 17, or that the above mentioned detection means are provided.

Also, a combination of both, step S100 and S101, is possible. For example, a (pre-stored) data base containing the different data set each being associated to a different biopsy needle 17 (biopsy unit 15) could be provided beforehand according to step S101, e.g. from a manufacturer, and the geometric data of the biopsy unit 15 is derived by means of the calibration procedure described in step S100.

Having the geometric data available, the breast is prepared with compression using the compression plate 13, as indicated by step S102. Thereafter, a scout-tomo-scan is conducted in step S103 without the biopsy unit 15 (without biopsy needle holder 16 or biopsy needle 17) in the X-ray beam. During this scout-tomo-scan a 3D model of the breast is acquired according to the above described steps S200, S201 and S202, wherein in steps S200 and S201 the "selected images" can again be images from all angular positions the image acquisition device is able to take. With the reconstructed 3D model achieved in step S202, the processor 18 is able to reconstruct/derive 2D slice images, wherein the 2D slice images are sectional images through the breast preferably in parallel to the xy-plane at different z positions. These 3D volume data are provided in step S205 for the viewing module. Several slice/slab images in parallel to the xy-plane at different z positions are displayed in steps S104 and S206 on the display 19, where the user can, in step S105 and S209, select the slice image showing the lesion best and identify the z-position of the lesion, i.e. by choosing a slice image reconstructed at a certain z-position, the z-position of the lesion is known. This choice of the best slice can be easily realized for example by scrolling a scroll wheel of a computer mouse and by clicking when the desired one is reached. For larger lesions, the displayed volume can be enlarged by combining some adjacent slices into a slab. In the selected slice/slab, the user can mark the x- and y-position of the lesion by positioning cross-hairs displayed on the display 19 with the help of the input device 20 over the center of the lesion. This has the benefit that only one crosshair cursor is necessary for defining the x and y position, since only one xy-view at a certain z-position is necessary. This minimizes the confusion that could be caused by selecting the position based on a right and left projection image, as necessary in stereoscopic imaging.

At this point, i.e. in step S210 or after S105, the coordinates of the lesion are known. This is the region of interest for the conducted biopsy.

Additionally to marking the lesion only in one slice showing a xy-view of the selected slice/slab, there could be provided the steps S207 and S208. In step S207, an xz-view of the selected slice/slab is shown, and in step S208, an yz-view of the selected slice/slab is shown, wherein in step S209 the lesion can be marked additionally in the views provided by steps S207 and S208 such that the region of interest is marked in three dimensions.

Both ways provide the actual x, y and z coordinates of the position of the biopsy unit 15 in step S210.

At step S106, the desired position of the biopsy needle 17 can be calculated by the controller 23 (the processor 18) from the known coordinates of the region of interest, and in step S107 the biopsy needle 17 can be positioned under control of the controller 23 (see FIG. 6) into the right position. The correctness of the positioning of the biopsy needle 17 can be verified with another tomosynthesis scan with limited number of angular positions along the trajectory of the X-ray source 11.

Knowing the 3D model of the biopsy unit 15 and having the actual position of the biopsy unit, the controller 23 can calculate in step S108 from the geometry model of the needle/needle holder the projection angles (angular positions) which will be in conflict with an image of the region of interest, i.e. which image would comprise a so called "needle shadow". In its simplest form this would be the determination in which angular positions the longitudinal direction of the X-ray source 11 intersects with the volume of the biopsy needle holder 16 or the biopsy needle 17. In step S108, there is the option to consider the compression plate 13 as no obstacle for the following tomosynthesis. This can be done in case the compression plate 13 is X-ray translucent. Alternatively, the compression plate 13 can be considered as unwanted in the X-ray beam and all focus positions (angular positions) can be excluded which would lead through the compression plate 13. These projection angles are excluded from the projection angles the image acquisition device is able to take, the remaining projection angles are the allowed projection angles. The list of allowed angulations or possible angular positions $\phi_1$, $\phi_2$, $\phi_3$, $\phi_N$ is provided in step S211.

In step S109, the number of remaining usable angular positions, the "allowed angular positions", is checked.

If the number is below a minimum, for example eight images, the routine proceeds to step S113, where it determines that no meaningful tomosynthesis can be executed. In this case, the user is recommended to use a stereoscopic/ stereotactic guidance instead of the tomosynthesis. In this connection, the controller 23 selects a pair of only two projections. The two projections have to meet the following properties: (a) there is no conflict with the "needle shadow" and (b) the left angular position of the X-ray source 11 is in the interval of [−25°; −10°], i.e. the angulation is between −25 and −10 degrees, and the right angular position of the X-ray source 11 is in the interval of [10°; 25°], i.e. the angulation is between 10 and 25 degrees with respect to the yz-plane. This procedure is still better than using the pre-defined, fixed angles of −15° and 15° as done in the stereography of the state of the art, and then realizing that one of the acquired images cannot be used due to a "needle shadow". The process for this stereoscopic guidance shall be explained shortly: From a previous examination (screening, diagnostic) a suspicious region has been identified containing a lesion or micro-calcifications. The exact location of this region is not known because the breast cannot be compressed in a reproducible way. A regular screening Mammogram (full size) is available from before. From this the location of the lesion is derived and it is tried to get it in the center of the small field-of-view of the following procedure. As a first step to prepare a biopsy examination, a first image of examination without angulation of the X-ray tube and with the compression plate already in place, but without a biopsy needle present, is taken, a so-called "scout image". A pair of stereoscopic images is taken and displayed in step S114. The lesion is marked with a crosshair cursor in the two images. From the coordinates the z-position of the lesion can be calculated by the processor. The needle is positioned and punched into the skin at the region of interest. The location of the needle tip (the active part of the needle can also be at the side of the needle) is checked in respect to the lesion. If the position is correct, the needle is activated and a tissue sample is taken in step S112. If necessary, the needle is re-positioned. Another stereoscopic imaging can verify that a certain tissue is no longer in the breast. A number of up to six or more stereoscopic examinations may be conducted in total.

If in step S109 the number of remaining usable angular positions is equal to or above a minimum, for example eight images, the routine proceeds to step S110 and it is determined that a meaningful 3D reconstruction for the purpose of biopsy guidance can be done. In this case, the allowed angular positions are provided in step S211 and the image acquisition device can make projection images according to the above described steps S200, S201 and S202, wherein the "selected angular positions" are in this case the allowed angular positions provided by step S211. Thus, projection images are made at all positions which are not in conflict with the biopsy unit, such that a needle shadow can be avoided on the projection images. In FIG. 2, the allowed angular positions are marked with crosses along the dotted trajectory of the X-ray source 11. Usually, a center area, next to the position in which the longitudinal direction of the X-ray source is in parallel to (coincidents with) the z-axis, is spared out from the allowed angular positions. Thus, usually a certain circular arc-shaped trajectory is remaining to the left and to the right of this center area, which may be non-symmetric. In the shown example of FIG. 2, there are eight allowed angular positions on the left and five on the right side. The resulting outermost longitudinal directions of the X-ray source 11 or the center beams are indicated by lines running from the outermost crosses to the center of the circular arc-shaped trajectory of the X-ray source 11. A 3D reconstruction of the data is done by the processor and the xy-plane, the yz-plane and the xz-plane of the slice/slab at the region of interest is displayed by the display 19 in step S111.

Based on the displayed slices, the user can verify that the biopsy needle 17 is in the vicinity of the lesion and can take the tissue sample ("fire the needle") in step S112.

Thereafter, another verification sample can show that (a part of) the lesion is no longer there. If this shows, that the lesion is still there, the routine can go back to step S107 and can be repeated in this manner several times.

It is explicitly intended that the teaching of this invention covers any combination of the above described embodiments.

While the invention has been illustrated and described in detail in the drawings and foregoing description, such illustration and description are to be considered illustrative or exemplary and not restrictive and it is not intended to limit the invention to the disclosed embodiments. The mere fact that certain measures are recited in mutually different dependent claims does not indicate that a combination of these measures cannot be used advantageously. Any reference signs in the claims should not be construed as limiting the scope of the invention.

LIST OF REFERENCE SIGNS

1 Shadow of biopsy needle holder
2 Shadow of biopsy needle
3 Shadow of opening of biopsy paddle
10 Medical tomosynthesis system
11 X-ray source
12 X-ray detector
13 Compression plate
14 Base frame
15 Biopsy unit
16 Biopsy needle holder
17 Biopsy needle
18 Processor
19 Display
20 Input device
21 Geometric data means
22 Opening
23 Controller
24 Tube movement unit
S100 Acquire 3D model of biopsy unit with X-ray imaging device
S101 Input 3D model of biopsy unit
S102 Compress breast with biopsy paddle
S103 Do scout tomo scan
S104 Display slices/slabs
S105 Mark lesion
S106 Calculate target needle position
S107 Position needle
S108 Calculate allowed angular positions for imaging
S109 Is number of allowed angular positions≥minimum?
S110 Do tomosynthesis at allowed angular positions
S111 Display slices
S112 Take tissue sample
S113 Do stereoscopic guidance
S114 Display projection images
S200 Expose selected images
S201 Acquire projection images at selected angular positions
S202 Do 3D reconstruction from the projection images
S203 Generate the 3D model of the biopsy unit from calibration image
S204 3D model of the biopsy unit
S205 3D volume data
S206 Show xy-view of slice/slab
S207 Show xz-view of slice/slab
S208 Show yz-view of slice/slab
S209 Select region of interest
S210 Actual xyz-position of the biopsy unit
S211 List of allowed angular positions

The invention claimed is:

1. A medical tomosynthesis system comprising:
a scanner configured for acquiring projection images of a subject volume from a plurality of respective projection angles around said subject volume, said plurality being from among a first set of projection angles at which said scanner is enabled for image acquisition, said acquiring being associated with corresponding fields of view, a part of a medical tomosynthesis apparatus being within a field of view from among said fields of view, said medical tomosynthesis apparatus including a medical tomosynthesis biopsy apparatus; and
an image processor configured to:
derive geometric data from a three-dimensional (3D) model of said part;
derive an actual position of said part;
from both said geometric data and said actual position, calculate a plurality of angular positions corresponding to projection angles of said first set in deciding which of said corresponding projection angles are in conflict with an image of a region of interest; and
exclude the projection angles decided to be in conflict in forming a second set of allowed projection angles,
wherein said system is configured to operate said scanner so as to confine, to projection angles within said second set, acquisition of projection images for use in tomosynthesis reconstruction.

2. A medical tomosynthesis system according to claim 1, wherein said processor is adapted for, when said actual position changes, again performing the deciding, this time from both said geometric data and a changed actual position, to update said second set.

3. A medical tomosynthesis system according to claim 1, wherein said processor is adapted to determine, depending on the number of angular positions from among the plurality of calculated angular positions, whether to conduct stereoscopic imaging or tomosynthetic imaging at the allowed projection angles.

4. A medical tomosynthesis system according to claim 1, wherein said part is at least one of a biopsy needle holder and a biopsy needle.

5. A medical tomosynthesis system according to claim 1, wherein said part comprises a compression plate for compressing said subject volume.

6. A medical tomosynthesis system according to claim 1, wherein said geometric data define an outer shape of said part.

7. The system of claim 1, wherein the excluding is from said corresponding projection angles.

8. The system of claim 1, said second set comprising the only angles allowed for tomosynthesis by said system.

9. The system of claim 1, further comprising a 3D reconstruction module configured for said tomosynthesis reconstruction.

10. The system of claim 1, wherein the operating is with said part in said actual position.

11. The system of claim 1, wherein said geometric data comprises geometric data of at least one of a biopsy needle and a biopsy needle holder.

12. The system of claim 1, wherein the deciding, for a given one of said corresponding projection angles, is based on whether a needle shadow appears in an image of said region of interest in imaging taken at said given one of said corresponding projection angles.

13. The system of claim 1, a location of at least one of a lesion and a micro-calcification serving as said region of interest.

14. A medical tomosynthesis system according to claim 1, further comprising a plurality of parts of a medical tomosynthesis apparatus,
wherein said part is from among said parts;
wherein said parts differentiate from each other at least partially with respect to their geometric data;
wherein said medical tomosynthesis system is configured to attachably hold one out of the plurality of parts in an interchangeable manner; and
wherein said medical tomosynthesis system is adapted to adapt said geometric data to the attached part out of said plurality of parts.

15. A medical tomosynthesis system according to claim 14, wherein said medical tomosynthesis system is adapted to detect which part from among said plurality of parts is attached to said medical tomosynthesis system, and is adapted to provide said processor with a stored data set of geometric data associated with the attached part.

16. The system of claim 14, wherein said geometric data of a respective part from among said parts is derived from a three-dimensional (3D) model of said respective part and comprises geometric data of at least one of a biopsy needle and a biopsy needle holder.

17. The system of claim 1, configured for using only projection images taken at projection angles from among said second set in forming an image volume, for deriving, from said image volume, multiple sectional images of respectively different imaging depths, and for determining, based on image-feature similarity, from said multiple sectional images, a depth of said region of interest.

18. The system of claim 17, wherein said determining selects a depth from among said depths.

19. The system of claim 1, further comprising said medical tomosynthesis apparatus.

20. The system of claim 19, serving as said medical tomosynthesis apparatus.

21. The system of claim 1, further configured for, via said image processor, computing said 3D model.

22. The system of claim 21, wherein the computing entails reconstructing said model from projection images acquired via said scanner.

23. The system of claim 1, wherein the deciding entails determining, for which of said corresponding projection angles, a longitudinal direction of an X-ray source intersects with said part.

24. The system of claim 23, said scanner comprising said X-ray source, and an X-ray detector for receiving X-rays emitted by said source.

25. A method for acquiring medical images, comprising the steps of:
acquiring projection images of a subject volume from a plurality of respective projection angles around said subject volume, said plurality being from among a first set of projection angles at which a scanner for said acquiring is enabled for image acquisition, said acquiring being associated with ti-corresponding fields of view, a part of a medical tomosynthesis apparatus being within a field of view from among said fields of view, said medical tomosynthesis apparatus including a medical tomosynthesis biopsy apparatus;
deriving geometric data from a three-dimensional (3D) model of said part;
deriving an actual position of said part;
from both said geometric data and said actual position, calculate a plurality of angular positions corresponding to projection angles of said first set in deciding which of said corresponding projection angles are in conflict with an image of a region of interest;
excluding the projection angles decided to be in conflict in forming a second set of allowed projection angles; and
operating said scanner so as to confine, to projection angles within said second set, acquisition of projection images for use in tomosynthesis reconstruction.

26. The method according to claim 25, further comprising the step of, when a position of said part changes, updating said second set by again deciding, from both said geometric data and said actual position, which of said corresponding projection angles are in conflict with said image and excluding said angles decided to be in conflict.

27. A non-transitory computer readable medium embodying a computer program for acquiring medical images, said program having instructions executable by a processor for performing a plurality of acts, from among said plurality there being the acts of:
acquiring projection images of a subject volume from a plurality of respective projection angles around said subject volume, said plurality being from among a first set of projection angles at which a scanner for said acquiring is enabled for image acquisition, said acquiring being associated with ti-corresponding fields of view, a part of a medical tomosynthesis apparatus being within a field of view from among said fields of view, said medical tomosynthesis apparatus including a medical tomosynthesis biopsy apparatus;
deriving geometric data from a three-dimensional (3D) model of said part;
deriving an actual position of said part;
from both said geometric data and said actual position, calculate a plurality of angular positions corresponding to projection angles of said first set in deciding which of said corresponding projection angles are in conflict with an image of a region of interest;
excluding the projection angles decided to be in conflict in forming a second set of allowed projection angles; and
operating said scanner so as to confine, to projection angles within said second set, acquisition of projection images for use in tomosynthesis reconstruction.

28. The computer readable medium of claim 27, a location of at least one of a lesion and a micro-calcification serving as said region of interest.

29. A medical tomosynthesis system comprising:
an X-ray source and an X-ray detector;
an image acquisition circuit configured for, via respective locations of said source and said detector, acquiring, in a plurality of angular positions around a subject volume, X-ray images of said subject volume;
a medical tomosynthesis biopsy apparatus disposed such that at least part of said medical tomosynthesis biopsy apparatus intervenes into said subject volume; and a processing circuit configured for:
> providing geometric data of said at least part of said medical tomosynthesis biopsy apparatus;
> knowing a three-dimensional (3D) model of said at least part of said medical tomosynthesis biopsy apparatus and having an actual position of said at least part of said medical tomosynthesis biopsy apparatus, calculating, from said geometric data, projection angles which are in conflict with an image of a region of interest within said volume; and
> excluding these projection angles from the projection angles the image acquisition circuit is able to take, such that a remaining set of projection angles, for which a corresponding plurality of angular positions is calculated in said calculating, is characterizable as the projection angles that are allowed.

30. The system of claim 29, wherein said processing circuit is further configured for deriving said geometric data from a three-dimensional (3D) model of said at least part of said medical tomosynthesis biopsy apparatus.

31. The system of claim 30, comprising a scanner that includes said X-ray source, said X-ray detector, said image acquisition circuit, and said medical tomosynthesis biopsy apparatus.

32. The system of claim 31, configured to operate said scanner so as to confine, to the allowed projection angles, acquisition of projection images for use in tomosynthesis reconstruction.

* * * * *